US006985611B2

(12) United States Patent
Loussouarn et al.

(10) Patent No.: US 6,985,611 B2
(45) Date of Patent: Jan. 10, 2006

(54) SYSTEM AND PROCESS FOR THE ANALYSIS AND PREDICTIVE SIMULATION OF THE EVOLUTION OF A HAIR REGION, AND MORE PARTICULARLY OF THE HUMAN SCALP

(75) Inventors: Geneviève Loussouarn, Clichy (FR); Catherine Huber, Paris (FR); Mahmoud Mourad, Paris (FR)

(73) Assignee: L'Oreal, Paris (FR)

( * ) Notice: Subject to any disclaimer, the term of this patent is extended or adjusted under 35 U.S.C. 154(b) by 511 days.

(21) Appl. No.: 09/731,970

(22) Filed: Dec. 8, 2000

(65) Prior Publication Data

US 2001/0017936 A1   Aug. 30, 2001

(30) Foreign Application Priority Data

Dec. 21, 1999   (FR)   .................. 99 16171

(51) Int. Cl.
    *G06K 9/00*   (2006.01)
(52) U.S. Cl. ...................... 382/128; 128/922
(58) Field of Classification Search ............... 382/128; 128/922; 250/461.2; 356/39, 40, 41, 42; 377/10, 11, 12
    See application file for complete search history.

(56) References Cited

U.S. PATENT DOCUMENTS

| 5,060,171 A | 10/1991 | Steir et al. |
| 5,331,472 A | 7/1994 | Rassman |
| 5,764,233 A | 6/1998 | Brinsmead et al. |
| 5,777,619 A * | 7/1998 | Brinsmead ................... 345/419 |
| 6,162,212 A * | 12/2000 | Kreindel et al. ............... 606/9 |
| 6,389,150 B1 * | 5/2002 | Amornsiripanitch ........ 382/100 |
| 6,581,011 B1 * | 6/2003 | Johnson et al. ............... 702/19 |
| 6,651,008 B1 * | 11/2003 | Vaisberg et al. .............. 702/21 |
| 2001/0006555 A1 | 7/2001 | Loussouarn |

FOREIGN PATENT DOCUMENTS

| EP | 0 092 075 | 10/1983 |
| EP | 0 725 364 A2 | 8/1996 |

OTHER PUBLICATIONS

Liposcak et al, "Face Recognition from Profiles Using Morphological Operations", Proceedings International Workshop on Recognition, Analysis, and Tracking of Faces and Gestures in . . . ICCV'99 (CAT. No. PR00378), Corfu, Greece Sep. 26-27, 1999, pp. 47-52, XP002152958, 1999, Los Alamitos, CA, USA, IEEE Comput. Soc, USA, ISBN: 0-7695-0378-0.

(Continued)

*Primary Examiner*—Samir Ahmed
*Assistant Examiner*—Anand Bhatnagar
(74) *Attorney, Agent, or Firm*—Nixon & Vanderhye P.C.

(57) ABSTRACT

System for the simulation of the evolution of a hair region of the scalp of a subject over time, comprising a means of observation of the said hair region able to output observation data, a first processing means capable of classifying the hairs of the said region on the basis of the observation data and of external data, a second processing means capable of simulating the evolution of the hairs as a function of the data emanating from the first processing means, and a means of displaying the data emanating from the second processing means.

12 Claims, 1 Drawing Sheet

OTHER PUBLICATIONS

Daldegan et al, "Creating Virtual Fur and Hair Styles for Synthetic Actors", Communicating with Virtual Worlds, Proceedings of Computer Graphics International '93, Lausanne, Switzerland, Jun. 21-25, 1993, pp. 358-370, XP000961750, 1993, Tokyo, Japan, Springer-Verlag, Japan, ISBN: 4-431-70125-7.

Courtois et al, British Journal of Dermatology, 1996, vol. 134, pp. 47-54.

* cited by examiner

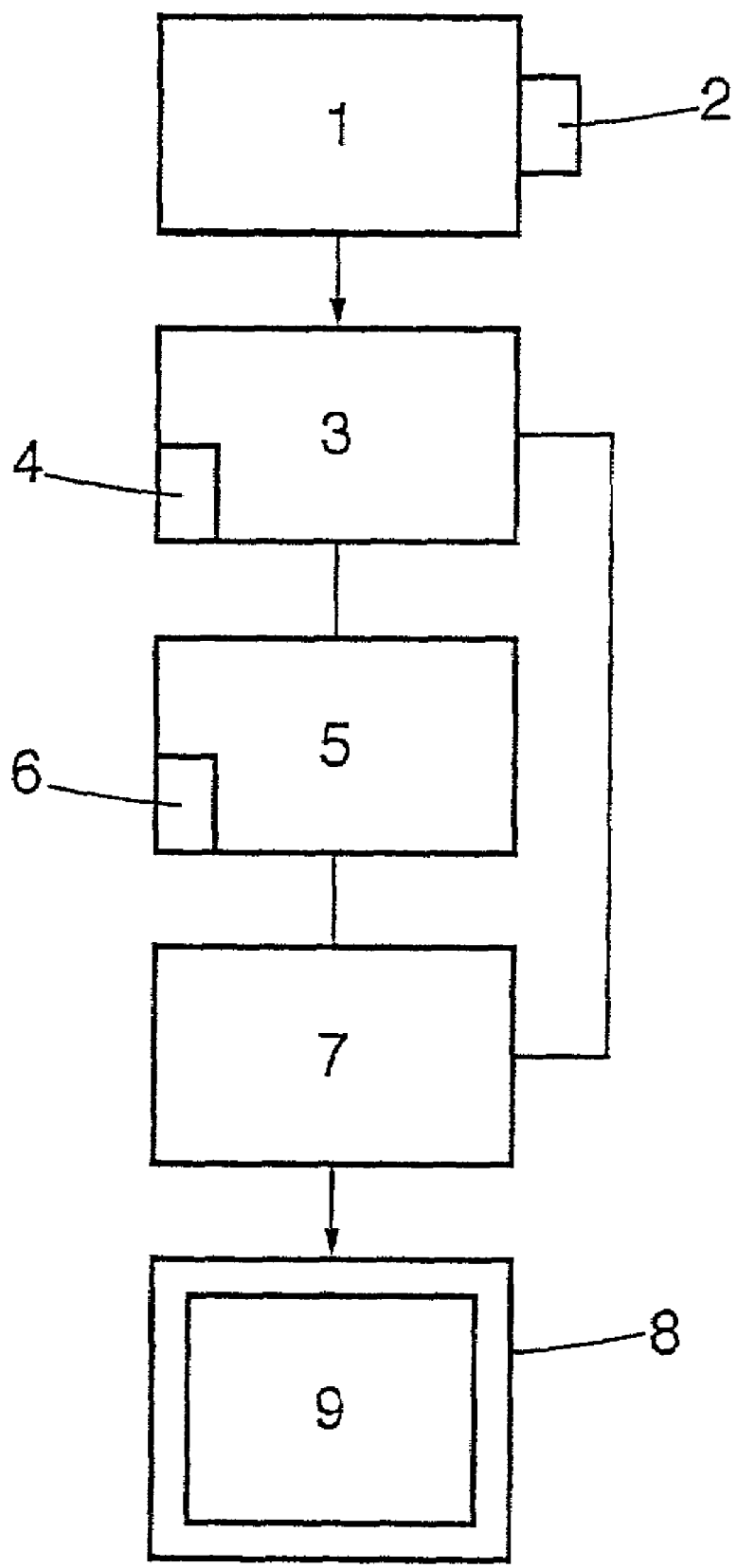

SYSTEM AND PROCESS FOR THE ANALYSIS AND PREDICTIVE SIMULATION OF THE EVOLUTION OF A HAIR REGION, AND MORE PARTICULARLY OF THE HUMAN SCALP

The present invention relates to the field of cosmetics and more particularly to the evolution of the human head of hair over the course of a lifetime.

The phenomenon of hair growth and loss in the human species, more particularly in the male sex, is complex and differs from animal species through at least two criteria:
- there are very few animal species which, with age, progressively lose their fur;
- animal species may experience seasonal moulting on account of the fact that the cycles of the strands are synchronized, that is to say all the strands grow or are lost at the same time.

In man, the hairs are generated by the hair follicles implanted in the scalp. A healthy head of hair is said to contain between 100 000 and 150 000 hairs, and each hair within this head of hair possesses its own cycle.

This life cycle is broken down into three generally successive physiological phases:
- a phase of hair growth, referred to as Anagen (A), which may last from a few weeks to 10 years,
- a transient phase of involution of the follicle and ceasing of hair growth with degeneration of the root, known as Catagen, of the order of a few weeks,
- a phase of shedding of the hair with the root moving up towards the surface, known as Telogen (T), lasting 1 to 5 months.

At the end of this last phase, the hair therefore disappears from the scalp and this disappearance may extend from a few days to a few months before the follicle is reactivated to give a new hair in the anagen growth phase.

After a certain number of cycles, the follicle permanently ceases its production and the hair may be regarded as Dead (Dd).

Given the ratio of the durations of the various phases of the life cycle of the hair, in practice, the Catagen phase the shortest is rarely observed; this is why the person skilled in the art prefers to reckon the Anagen (A), Telogen (T) and Disappeared (D) phases.

The phenomenon of ageing, over the course of a lifetime, leads over tens of years to a shortening of the growth phases (A) and consequently to an increase in the proportion of the hairs in the loss phase (T). This phenomenon may be accelerated in the case of alopecia which more particularly afflicts men but also women, and which in its final stage leads to baldness, or total shedding of the head of hair.

Since the phases of the hair cycle unravel over long durations, especially the growth phase (A), it follows that the observation of the state of the hairs of a region of the scalp at a precise instant constitutes merely an instantaneous measurement which cannot forecast the future evolution.

Specifically, the current state of the art does not make it possible by observing and quantifying the state of the hair of a young 25-year-old person to forecast and/or illustrate what the state of his head of hair will be when he reaches 60 years of age.

The aim of the present invention is to simulate the chronological evolution of a head of hair on the basis of the smallest possible number of measurements.

The system, according to the invention, is intended for the simulation of the evolution of a region of the scalp of a subject over time, and whose extension to the entire scalp makes it possible to illustrate the overall evolution of the head of hair.

The system comprises a means of observation of the said hair region able to output digital observation data, a first digital data processing means capable of classifying elementary parts of the said region on the basis of the observation data and of external data, a second digital data processing means capable of simulating the evolution of the said hair region as a function of the data emanating from the first digital data processing means, and a means of displaying the data emanating from the second digital data processing means. The data output by the first processing means comprise at least one classification according to the diameter of the hairs.

Advantageously, the data output by the first processing means comprise the distribution of the hairs according to whether they are in the Anagen, Telogen or Disappeared phase, as a function of their diameters. The hairs can be classified into five diameter ranges for the Anagen and Telogen phases.

In one embodiment of the invention, the external data comprise at least the age of the subject.

Advantageously, the second processing means is capable of calculating the proportion A of hairs in the Anagen phase.

In one embodiment of the invention, the second processing means is capable of calculating and predicting comprise the surface density of hairs, the proportion T of hairs in the Telogen phase, the proportion D of Disappeared hairs, and the individual rate of growth of the hairs.

The system can comprise a means for performing a third processing for simulating the evolution of the entire head of hair of the subject on the basis of the data emanating from the second processing.

In one embodiment of the invention, the system comprises a means for associating data simulating the evolution of the face with the data emanating from the third processing.

In one embodiment of the invention, the second processing means comprises a means for estimating the number of cycles $n_c$ performed by an observed hair on the basis of the subject's age, and for comparing it with a predetermined maximum number of cycles $N_k$, a cycle being defined by the successive passage through the three phases, Anagen, Telogen and Disappeared.

The subject of the invention is also a process for the simulation of the evolution of a hair region of the scalp of a subject over time, in which:
- the said hair region is observed so as to provide observation data,
- a first processing of the observation data is performed so as to classify hairs of the said hair region on the basis of the observation data and of external data,
- a second processing is performed so as to perform a simulation of the temporal evolution of the said hairs as a function of the data emanating from the first processing means, and
- data emanating from the second processing are displayed.

The data output by the first processing means comprise at least a classification according to the diameter of the hairs.

It is conceivable to classify the hairs in tufts and to calculate a mean number of hairs per tuft. A number can be assigned to each hair and to each tuft.

In one embodiment of the invention, at least one observation is performed, each observation being preceded by a step of shaving the said hair region, the shaving step being separated from the corresponding observation by a first given duration.

In one embodiment of the invention, at least two observations are performed, separated by a second given duration.

Advantageously, on the basis of the observation data, the hair coverage is calculated as a function of the number, the diameter and the length or the rate of growth of the hairs.

Advantageously, a third processing is performed so as to perform a simulation of the evolution of the entire head of hair of the subject on the basis of the data emanating from the second processing and the data emanating from the third processing are displayed. The displaying of the said data emanating from the third processing can be performed by flat projection, for example by a projection of the type used in cartography, in particular a conical Lambert projection. Data from simulating the evolution of the face can be associated with the data emanating from the third processing and the associated data can be displayed.

In one embodiment of the invention, the evolution of a hair region that has undergone a surgical, aesthetic or medical intervention is simulated.

The observation data can emanate from any appropriate means for collecting photographic and videographic images, analogue or digital, or any other imaging means obtained through a noninvasive, physiology-friendly route not requiring special preparation of the scalp.

In one embodiment of the invention, a hair is assigned a total duration of continuation in its current phase, a random draw of the duration elapsed in the said phase is performed, and the remaining duration in the said phase is calculated, as equal to the difference between the total duration of continuation and the duration elapsed. The assigning of the total duration of continuation may be performed according to a compound Cox law and can take account of the diameter of the hair, the proportion of hairs in the Anagen phase, the density of hairs, the mean number of hairs per tuft, the cycle number, etc.

Stated otherwise, the simulation system associates the establishing of initial observation data, on the basis of a region of small area, regarding the number of hairs, the proportions of the latter in each phase, the age of the subject, and the mathematical modelling of these which makes it possible to extend the evolution of each parameter to the short medium or very long term. The state of the head of hair can thus be simulated over various durations of between 3 months and 100 years.

The present invention will be better understood on studying the detailed description of a few embodiments taken by way of wholly non-limiting examples and illustrated by the appended drawing.

FIG. 1 is a diagrammatic view of the simulation system in accordance with the invention.

As may be seen in this figure, the simulation system in accordance with the invention comprises a camera 1, for example of CCD type, equipped with an objective 2, intended for observing a specified hair region, for example a region of 1 cm². The system also comprises a classification means 3 receiving the digital data emanating from the camera 1. The classification means 3 is provided with a memory 4 allowing among other things the storage of the said data originating from the camera 1. The classification means 3 is capable of determining the Anagen, Telogen or Disappeared phase, in which is a hair present in an elementary part of the observed hair region, and the diameter of each hair.

Stated otherwise, the classification means 3 receives as input an image file representative of the hair region observed and in which each elementary zone is assigned a grey level or colour characteristics, and outputs a file in which each hair is assigned a state, anagen, telogen or disappeared and possibly other characteristics, in particular relating to tufts or clumps of hairs.

The simulation system comprises a simulation means 5 provided with a memory 6 and linked to the classification means 3 so as to receive the classified data comprising in particular the two-dimensional coordinates of a hair follicle, the current phase of the corresponding hair together with the rate of growth of the said hair. The classification means 3 can also transmit to the simulation means 5, data relating to the surface density of hair, to the proportion A of hairs in the anagen phase, to the proportion T of hairs in the telogen phase, and to the proportion D of hairs in the Disappeared phase.

The simulation means 5 is capable of outputting data for forecasting the individual state of each hair at a future instant. Stated otherwise, the simulation means 5 provides a file containing the coordinates of a hair follicle, the phase which the corresponding hair will be in at a future date, and the date for which the simulation was carried out.

The system furthermore comprises a means 7 for generalizing the simulation to the entire head of hair of a user. On the basis of the simulation data originating from the simulation means 5, of which the data generally relate to only a small area, for example of the order of 1 cm², the generalization means 7 is able to output data similar to those provided by the simulation means 5 but covering a larger expanse desired by the user, for example the entire scalp. The generalization means 7 also receives data originating from the classification means 3 insofar as the camera 1 will, for the purpose of the generalization, capture at least one general image of the area in respect of which one wishes to perform the generalization, in particular the scalp, so as to be able to extend the results of the simulation to this larger area.

A display means 8 such as a monitor 9, provided with a screen 9, is linked to the generalization means 7 so that the user can see the results of the simulation just performed. A printer, not represented, could also be provided and linked to the generalization means 7.

The possible evolution of the phases of a hair is as follows: a given hair which is in the Anagen phase, that is to say the growth phase, may, in the course of a given elementary duration, remain in this same phase or evolve to a Telogen phase or ceasing of growth phase. The passage of the hairs from the Anagen phase to the Telogen phase is a phenomenon which can be analysed statistically. The hairs remain in the Telogen phase and then normally evolve to the Disappeared phase. Thereafter, the hairs normally evolve either to a new Anagen phase, or to a death phase in which they remain permanently.

The term "cycle" is here understood to mean the passage of a follicle through the three phases, Anagen, Telogen and Disappeared, with return to the anagen phase. However, if one of these three phases is of short duration, it may be difficult to observe it. The simulation means takes account thereof by providing for possible direct transitions A→D, T→A or else D→T.

With each hair there are associated a certain number of variables making it possible to tag it and to model its evolution, in particular: number of the hair, number of the tuft to which the hair belongs, diameter of the hair, number of cycles already performed. On the basis of these data charted over an elementary region of known area, the density of hairs, the proportion of hairs in the Anagen phase, the richness of the tufts or the mean number of hairs per tuft, etc. are calculated. The hairs in the Anagen and Telogen phases are classified by diameter.

It is thus possible to provide five classes of diameter for the Anagen phase and five classes of diameter for the Telogen phase, the Disappeared phase being regardable as a zero diameter.

The modelling of the evolution of a hair over time involves establishing the law for the duration of each of the phases of the cycle, and in particular for the duration TA of the Anagen phase, and also transition matrices for transferring between the eleven states of the hair. The durations of the Telogen and Disappeared phases are denoted $T_T$ and $T_D$ respectively.

The law for the duration of the Anagen phase is established firstly by calculating three parameters a, b, c relating to the alopecia of the subject:

a=1 if the density of hairs per cm² is greater than or equal to 270, otherwise a=0;
b=1 if the proportion of Anagens, the ratio of the number of anagen hairs to that of hairs present, is greater than or equal to 0.8, otherwise b=0;
c=2−min(a,b),c=1 if the subject is regarded as normal, and 2 if regarded as alopecic.

Denoting the diameter of the hair by d, a Cox model for the law for the duration of the anagen phase gives an effect of the four variables a, b, c and d, with a Weibull law as base law. The probability that the duration of the Anagen phase is equal to or greater than a value t is, for a hair of diameter d, over a site with alopecia parameters a, b and c:

$$P(T_A \geq t|a,b,c,d) = \exp(-(\lambda t)^\alpha)$$

with $$\alpha = 1 - 1/(5-c) \text{ and } \lambda = \exp(2-(a+b)/2 - 0.7*d - |d-3|*0.3)$$

The negative coefficient relating to the diameter indicates a lengthening of the Anagen phase for hairs of large diameter, and quantifies the impact of an increase in diameter on the deceleration of the anagen phase of the cycle.

The Telogen and Disappeared phases have a behaviour which is far less differentiated between normal sites and alopecic sites.

The duration of the Telogen phase T can be modelled by a Weibull law with parameter α=1.8 and λ=exp(−1.4+0.2*a), and that of the disappeared phase by an exponential (α is not significantly different from 1) with parameter λ=exp(−1+0.2*a).

The phase transition matrices group together the probabilities of passing from a state at an instant t to a state at an instant t+1, conditionally upon the fact that a change of phase has occurred between the instants t and t+1.

Three matrices are used depending on whether the hair is leaving the Anagen, Telogen or Disappeared phase. These matrices have the following values, given a confidence interval of around 2%:

Transition matrix for going from the Anagen phase for normal subjects

|    | D    | T1   | T2   | T3   | T4   | T5   |
|----|------|------|------|------|------|------|
| A1 | 0.27 | 0.71 | 0.02 | 0.00 | 0.00 | 0.00 |
| A2 | 0.10 | 0.10 | 0.75 | 0.05 | 0.00 | 0.00 |
| A3 | 0.04 | 0.00 | 0.14 | 0.79 | 0.03 | 0.00 |
| A4 | 0.04 | 0.00 | 0.07 | 0.36 | 0.53 | 0.00 |
| A5 | 0.08 | 0.00 | 0.00 | 0.08 | 0.50 | 0.34 |

Transition matrix for going from the Anagen phase for alopecic subjects

|    | D    | T1   | T2   | T3   | T4   | T5   |
|----|------|------|------|------|------|------|
| A1 | 0.17 | 0.79 | 0.04 | 0.00 | 0.00 | 0.00 |
| A2 | 0.06 | 0.09 | 0.76 | 0.09 | 0.00 | 0.00 |
| A3 | 0.05 | 0.00 | 0.15 | 0.75 | 0.05 | 0.00 |
| A4 | 0.03 | 0.00 | 0.03 | 0.24 | 0.62 | 0.08 |
| A5 | 0.03 | 0.00 | 0.00 | 0.09 | 0.29 | 0.59 |

Transition matrix for going from the Telogen stage for normal subjects

|    | D    | A1   | A2   | A3   | A4   | A5 |
|----|------|------|------|------|------|----|
| T1 | 0.91 | 0.07 | 0.02 | 0.00 | 0.00 | 0  |
| T2 | 0.86 | 0.03 | 0.08 | 0.03 | 0.00 | 0  |
| T3 | 0.83 | 0.02 | 0.03 | 0.12 | 0.00 | 0  |
| T4 | 0.85 | 0.00 | 0.00 | 0.06 | 0.09 | 0  |
| T5 | 0.60 | 0.00 | 0.00 | 0.20 | 0.20 | 0  |

Transition matrix for going from the Telogen state for alopecic subjects

|    | D    | A1   | A2   | A3   | A4   | A5   |
|----|------|------|------|------|------|------|
| T1 | 0.78 | 0.19 | 0.03 | 0.00 | 0.00 | 0.00 |
| T2 | 0.72 | 0.08 | 0.17 | 0.03 | 0.00 | 0.00 |
| T3 | 0.73 | 0.06 | 0.08 | 0.11 | 0.02 | 0.00 |
| T4 | 0.70 | 0.06 | 0.07 | 0.06 | 0.11 | 0.00 |
| T5 | 0.78 | 0.05 | 0.03 | 0.02 | 0.03 | 0.09 |

Transition matrix for going from the Disappeared state for normal subjects

|    | A1  | A2  | A3   | A4   | A5   | T1   | T2   | T3   | T4   | T5   |
|----|-----|-----|------|------|------|------|------|------|------|------|
| D1 | 0.8 | 0.1 | 0.03 | 0.02 | 0.00 | 0.05 | 0.00 | 0.00 | 0.00 | 0.00 |
| D2 | 0.2 | 0.5 | 0.24 | 0.04 | 0.00 | 0.00 | 0.00 | 0.00 | 0.00 | 0.00 |
| D3 | 0.1 | 0.2 | 0.62 | 0.08 | 0.00 | 0.00 | 0.00 | 0.00 | 0.00 | 0.00 |
| D4 | 0.2 | 0.1 | 0.31 | 0.37 | 0.02 | 0.00 | 0.00 | 0.00 | 0.00 | 0.00 |
| D5 | 0.0 | 0.0 | 0.67 | 0.33 | 0.00 | 0.00 | 0.00 | 0.00 | 0.00 | 0.00 |

Transition matrix for going from the Disappeared state for alopecic subjects

|    | A1   | A2   | A3   | A4   | A5   | T1   | T2   | T3   | T4   | T5   |
|----|------|------|------|------|------|------|------|------|------|------|
| D1 | 0.77 | 0.1  | 0.02 | 0.00 | 0.00 | 0.11 | 0.00 | 0.00 | 0.00 | 0.00 |
| D2 | 0.27 | 0.59 | 0.10 | 0.02 | 0.00 | 0.00 | 0.02 | 0.00 | 0.00 | 0.00 |
| D3 | 0.16 | 0.3  | 0.46 | 0.06 | 0.02 | 0.00 | 0.00 | 0.00 | 0.00 | 0.00 |
| D4 | 0.13 | 0.2  | 0.24 | 0.34 | 0.09 | 0.00 | 0.00 | 0.00 | 0.00 | 0.00 |
| D5 | 0.06 | 0.1  | 0.21 | 0.15 | 0.48 | 0.00 | 0.00 | 0.00 | 0.00 | 0.00 |

It will be noted that a fictitious diameter is assigned to the disappeared hairs. It is in fact the diameter they had immediately prior to their disappearance.

Comparison of the last two matrices shows a greater propensity to "direct" passage from the Disappeared state to the Telogen state, without observing passage through the Anagen state, of the hairs of alopecic sites, this happens for example to around 10% of the very fine hairs of diameter 1, as against around 5% in normal subjects.

The number of complete cycles performed by each hair can also be taken into account in the model. If a hair has reached a critical number of cycles $N_k$, it dies and never regrows. $N_k$ is, in general, between 20 and 25, or even 27. It is therefore possible to model a progressive shortening of the duration of the Anagen phases on the basis of the number of cycles already performed by the hairs.

On the basis of a single observation, or even of two separate observations, a month apart for example, the hairs in the disappeared state are not observed. One therefore employs an estimate of the number of disappeared hairs which are estimated together with their diameter before disappearance and the proportion of the diameters of the hairs present, by virtue of the classification means 3.

For normal subjects, it is possible to take into account a mean percentage of disappeareds of around 20% and, for alopecic subjects, a mean percentage of disappeareds of around 35%. Fictitious hairs are therefore created in this way, making it possible to take account of the small number and/or of the short duration of the observations.

To further enhance the modelling, it is possible to calculate an index representative of the amount of coverage of the scalp by the hairs, stated otherwise of the visual impression given by the head of hair. This index is calculated by adding up the product for each of the states (A1, A2, A3, A4, A5, T1, T2, T3, T4, T5), of the number of hairs in the state (phase, diameter), of the diameter of the hairs and of the length of growth or of the rate of growth of the hairs.

In certain cases and depending on the subject's type of hairstyle, it would be conceivable to take into account the square of the diameter rather than the diameter, for example for a crew-cut type hairstyle.

For a given subject desiring a modelling of the evolution of his head of hair, one will perform a trichogram, or two trichograms separated by a specified duration, for example of the order of a month. Each trichogram is performed over an area of the order of a $cm^2$. The said area of a hair region is completely shaved and then, a few days later, for example two or three, a snapshot of the said area which was shaved is captured by means of the camera 1. It is thus possible, by virtue of the classification means, to determine which phase each hair is in. Specifically, the hairs in the Anagen phase will have grown appreciably, the hairs in the Telogen phase will not have grown or will hardly have grown, and the hairs in the disappeared phase will not be observed.

In the case of two trichograms, the second is performed in the same manner as the first, at the same place on the subject's skull.

By virtue of the invention, the user benefits from a forecast at different times, from a few months to a few tens of years and which can take into account rapid evolutions of the hair which cannot be observed in the data which served to establish the model. This forecast can also pertain to indirect parameters, such as the volume or the coverage of the head of hair in addition to the phase parameters.

What is claimed is:

1. System for the simulation and predictive analysis of the evolution of a hair region of the dermis of a subject over time, characterized in that it comprises a means of observation of the said hair region able to output digital observation data, a first digital data processing means capable of classifying the hairs of the said region on the basis of the observation data and of external data, a second digital data processing means capable of simulating the evolution of the hairs as a function of the data emanating from the first digital data processing means, and a means of displaying the data emanating from the second digital data processing means, the data output by the first digital data processing means comprising at least one classification according to the diameter of the hairs.

2. System according to claim 1, characterized in that the data output by the first processing means furthermore comprise a classification of the hairs according to whether they belong to the Telogen, Anagen or Disappeared phases.

3. System according to claim 1, characterized in that the external data comprise at least the age of the subject.

4. System according to claim 1, characterized in that the second processing means is capable of calculating the proportion A of hairs in the Anagen phase.

5. System according to claim 1, characterized in that the second processing means is capable of calculating and forecasting the surface density of hairs, the proportion T of hairs in the Telogen phase, the proportion D of Disappeared hairs, and the individual rate of growth of the hairs.

6. System according to claim 1, characterized in that it comprises a means for performing a third processing for simulating the evolution of the entire head of hair of the subject on the basis of the data emanating from the second processing.

7. System according to claim 6, characterized in that it comprises a means for associating data simulating the evolution of the face with the data emanating from the third processing.

8. Process for the simulation and predictive analysis of the evolution of a hair region of the scalp of a subject over time, in which:

the said hair region is observed so as to provide digital observation data, a first digital processing of the observation data is performed so as to classify hairs of the said hair region on the basis of the observation data and of external data, a second digital processing is performed so as to perform a simulation of the temporal evolution of the said hairs as a function of the data emanating from the first digital processing, and data emanating from the second digital processing are displayed, the data output by the first processing means comprising at least one classification according to the diameter of the hairs.

9. Process according to claim 8, in which at least one observation is performed, each observation being preceded by a step of shaving the said hair region, the shaving step being separated from the corresponding observation by a first given duration.

10. Process according to claim 9, in which at least two observations are performed, separated by a second given duration.

11. Process according to claim 8 in which, on the basis of the observation data, the hair coverage is calculated as a function of the number, the diameter and the length or the rate of growth of the hairs.

12. Process according to any claim 8 in which a third processing is performed so as to perform a simulation of the evolution of the entire head of hair of the subject on the basis of the data emanating from the second processing and the data emanating from the third processing are displayed.

* * * * *